(12) United States Patent
Huang et al.

(10) Patent No.: US 12,098,412 B2
(45) Date of Patent: Sep. 24, 2024

(54) ROSEBURIA HOMINIS HGM001 ISOLATE AND USE THEREOF

(71) Applicant: Food Industry Research and Development Institute, Hsinchu (TW)

(72) Inventors: Chien-Hsun Huang, Hsinchu (TW); Li-Wen Hsu, Hsinchu (TW); Jong-Shian Liou, Hsinchu (TW); I-Ching Chen, Hsinchu (TW); Sung-Yuan Hsieh, Hsinchu (TW); Chien-Chi Chen, Hsinchu (TW)

(73) Assignee: Food Industry Research and Development Institute, Hsinchu (TW)

( * ) Notice: Subject to any disclaimer, the term of this patent is extended or adjusted under 35 U.S.C. 154(b) by 135 days.

(21) Appl. No.: 17/717,678

(22) Filed: Apr. 11, 2022

(65) Prior Publication Data
US 2022/0356496 A1    Nov. 10, 2022

(30) Foreign Application Priority Data

May 6, 2021   (TW) .................................. 110116402

(51) Int. Cl.
    *C12P 7/52*      (2006.01)
    *A61P 1/04*      (2006.01)
    *A61P 43/00*     (2006.01)

(52) U.S. Cl.
    CPC .................. *C12P 7/52* (2013.01); *A61P 1/04* (2018.01); *A61P 43/00* (2018.01); *C12P 2201/00* (2013.01); *C12P 2203/00* (2013.01)

(58) Field of Classification Search
    CPC ..... C12P 7/52; C12P 2201/00; C12P 2203/00; A61P 1/04; A61P 43/00; A23L 33/125; A23L 33/135; C12R 2001/01; C12N 1/205
    See application file for complete search history.

(56) References Cited

U.S. PATENT DOCUMENTS 9,314,489 B2 *    4/2016   Kelly .................... A61K 35/74

OTHER PUBLICATIONS

Duncan SH, Aminov RI, Scott KP, Louis P, Stanton TB, Flint HJ.. Int J Syst Evol Microbiol. Oct. 2006;56(Pt 10):2437-2441. doi:10.1099/ijs.0.64098-0. PMID: 17012576. (Year: 2006).*
Machiels et al "A Decrease of the Butyrate-Producing Species *Roseburia hominis* and *Faecalibacterium prausnitzii* Defines Dysbiosis in Patients with Ulcerative Colitis". Gut. vol. 63(8). pp. 1-9. 2013.
Search Report issued in Taiwanese Patent Application No. 110116402 on Apr. 27, 2022.

* cited by examiner

*Primary Examiner* — Kade Ariani
(74) *Attorney, Agent, or Firm* — Morse, Barnes-Brown & Pendleton, P.C.; Martin Z. Zhang, Esq.; Russell L. Widom

(57) ABSTRACT

Disclosed herein is an isolated strain of *Roseburia hominis* HGM001, which is deposited at Deutsche Sammlung von Mikroorganismen and Zellkulturen GmbH under an accession number DSM 34119. A method for producing butyric acid using the isolated strain of *Roseburia hominis* HGM001, a fermented culture produced by the method, and a method for alleviating an inflammatory disorder using the fermented culture are also disclosed.

2 Claims, 4 Drawing Sheets

Specification includes a Sequence Listing.

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Forward primer 8F for PCR amplification of
      bacterial 16S rDNA fragment

<400> SEQUENCE: 1
ggagtttgat cctggctcag                                                 20

<210> SEQ ID NO 2
<211> LENGTH: 17
<212> TYPE: DNA
<213> ORGANISM: Artificial Sequence
<220> FEATURE:
<223> OTHER INFORMATION: Reverse primer 1540R for PCR amplification of
      bacterial 16S rDNA fragment

<400> SEQUENCE: 2
aaggaggtga tccagcc                                                    17
```

<210> SEQ ID NO 3
<211> LENGTH: 1480
<212> TYPE: DNA
<213> ORGANISM: ROSEBURIA HOMINIS

<400> SEQUENCE: 3

```
gatgaacgct ggcggcgtgc ttaacacatg caagtcgaac gaagcacttt aattgatttc      60
ttcggaatga agtttttgtg actgagtggc ggacgggtga gtaacgcgtg ggtaacctgc     120
ctcatacagg gggataacag ttggaaacga ctgctaatac cgcataagcg cacaggattg     180
catgatccag tgtgaaaaac tccggtggta tgagatggac ccgcgtctga ttagccagtt     240
ggcggggtaa cggcccacca aagcgacgat cagtagccga cctgagaggg tgaccggcca     300
cattgggact gagacacggc ccaaactcct acgggaggca gcagtgggga atattgcaca     360
atgggggaaa ccctgatgca gcgacgccgc gtgagcgaag aagtatttcg gtatgtaaag     420
ctctatcagc agggaagaag aatgacggta cctgactaag aagcaccggc taaatacgtg     480
ccagcagccg cggtaatacg tatggtgcaa gcgttatccg gatttactgg gtgtaaaggg     540
agcgcaggcg gtacggcaag tctgatgtga atcccgggg ctcaaccccg gtactgcatt     600
ggaaactgtc ggactagagt gtcggagggg taagtggaat tcctagtgta gcggtgaaat     660
gcgtagatat taggaggaac accagtggcg aaggcggctt actggacgat tactgacgct     720
gaggctcgaa agcgtgggga gcaaacagga ttagataccc tggtagtcca cgccgtaaac     780
gatgaatact aggtgtcggg gagcattgct cttcggtgcc gcagcaaacg caataagtat     840
tccacctggg gagtacgttc gcaagaatga aactcaaagg aattgacggg acccgcaca     900
agcggtggag catgtggttt aattcgaagc aacgcgaaga accttaccaa gtcttgacat     960
cccactgacm ragtatgtaa tgtactttct cttcggagca gtggtgacag gtggtgcatg    1020
gttgtcgtca gctcgtgtcg tgagatgttg ggttaagtcc cgcaacgagc gcaacccta    1080
ttcttagtag ccagcggttc ggccgggcac tctaggagaa ctgccaggga taacctggag    1140
gaaggtgggg atgacgtcaa atcatcatgc cccttatgac ttgggctaca cacgtgctac    1200
aatggcgtaa acaaagggaa gcaatcccgc gagggggagc aaatctcaaa ataacgtct    1260
cagttcggac tgtagtctgc aactcgacta cacgaagctg gaatcgctag taatcgcgaa    1320
tcagaatgtc gcggtgaata cgttcccggg tcttgtacac accgcccgtc acaccatggg    1380
agttggtaat gcccgaagtc agtgacccaa ccgcaaggag ggagctgccg aaggcaggac    1440
tgataactgg ggtgaagtcg taacaaggta gccgtatcgg                           1480
```

ROSEBURIA HOMINIS HGM001 ISOLATE AND USE THEREOF

CROSS-REFERENCE TO RELATED APPLICATION

This application claims priority of Taiwanese Invention Patent Application No. 110116402, filed on May 6, 2021.

FIELD

The present disclosure relates to an isolated strain of *Roseburia hominis* HGM001, which has been deposited at Deutsche Sammlung von Mikroorganismen and Zellkulturen GmbH under an accession number DSM 34119. The present disclosure also relates to a method for producing butyric acid using the isolated strain of *Roseburia hominis* HGM001, a fermented culture produced by the method, and use of the fermented culture for alleviating an inflammatory disorder.

BACKGROUND

Butyric acid is a short-chain fatty acid (SCFA) (also known as volatile fatty acid (VFA)), which may be produced by fermentation of indigestible carbohydrates (such as resistant starches and dietary fibers) by intestinal bacteria. Previous studies have reported that butyrate production is positively correlated with anti-inflammatory effects, and butyrate can modulate immune responses, promote intestinal barrier function, and alleviate inflammatory disorders (such as inflammatory bowel disease (IBD) and irritable bowel syndrome (IBS)) (Liu H. et al. (2018), *Adv. Nutr.*, 9:21-29; and Martin R. et al. (2017), *Front. Microbiol., doi:* 10.3389/fmicb.2017.01226).

Butyric acid can be synthesized by chemical methods and has been widely used in food, cosmetic, pharmaceutical and chemical industries. Since butyric acid exerts beneficial pharmacological effects, researchers in the pharmaceutical industry endeavor to develop methods for mass production of butyric acid so as to meet the high market demand. In this regard, microbial fermentation has advantages such as low cost, fast production rate, high safety, etc., and hence, is widely applied for producing butyric acid.

Previous studies have demonstrated that certain strains of *Faecalibacterium* spp., *Eubacterium* spp., *Roseburia* spp., *Coprococcus* spp., and *Clostridium* spp. are capable of producing butyric acid. For example, it has been reported in Duncan, S. H. et al. (2002), *Appl. Environ. Microbiol.*, 68:5186-5190 that *Roseburia intestinalis* L1-8151, *Roseburia* spp. strain A2-183, and *Roseburia* spp. strain A2-181 isolated from the human gut can produce high concentrations of butyrate in in vitro experiments (the butyrate concentrations achievable may be approximately 11.59 mM, 11.42 mM, and 11.01 mM, respectively).

In addition, WO 2017033925 A1 discloses that *Roseburia intestinalis* DSM 14610$^T$ and *Clostridium butyricum* JCM 1391$^T$ can produce high concentrations of butyric acid in in vitro experiments (the butyric acid concentrations achievable may be approximately 28.2 mM and 19.3 mM, respectively), while the butyric acid concentration achievable by *Roseburia hominis* DSM 16839$^T$ is only 1 mM.

In spite of the aforesaid, there is still a need to develop a new strategy that can be utilized for mass production of butyric acid.

SUMMARY

Therefore, in a first aspect, the present disclosure provides a method for producing butyric acid, which can alleviate at least one of the drawbacks of the prior art, and which includes cultivating an isolated strain of *Roseburia hominis* HGM001 in a culture medium containing a fermentable sugar. The isolated strain of *Roseburia hominis* HGM001 is deposited at Deutsche Sammlung von Mikroorganismen and Zellkulturen GmbH under an accession number DSM 34119.

In a second aspect, the present disclosure provides a fermented culture including butyric acid, which can alleviate at least one of the drawbacks of the prior art, and which is produced by the aforesaid method.

In a third aspect, the present disclosure provides a method for alleviating an inflammatory disorder, which can alleviate at least one of the drawbacks of the prior art, and which includes administering to a subject in need thereof a composition including the aforesaid fermented culture.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

Figure 1:
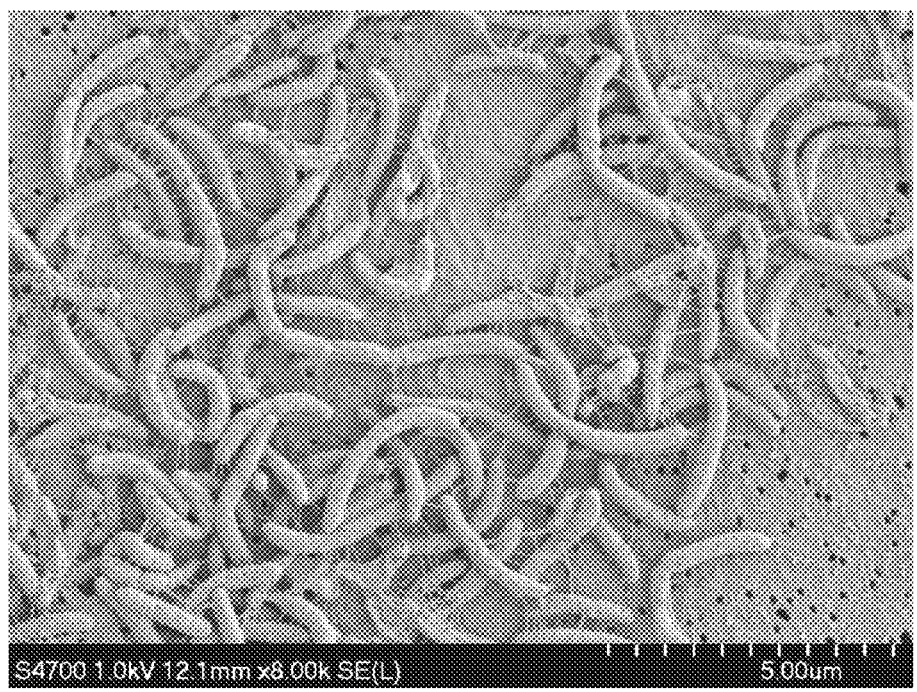
FIG. 1 shows a morphological analysis result of the enteric bacterial isolate HGM001.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

The present disclosure provides an isolated strain of *Roseburia hominis* HGM001, which was deposited at the Bioresource Collection and Research Center (BCRC) of the Food Industry Research and Development Institute (FIRDI) (No. 331, Shih-Pin Rd., Hsinchu City 300, Taiwan) on Apr. 20, 2021 and assigned accession number BCRC 911054, and which was also deposited on Jan. 10, 2022 at the Deutsche Sammlung von Mikroorganismen und Zellkulturen (DSMZ) GmbH (Inhoffenstr. 7B, D-38124 Braunschweig, Germany) in accordance with the Budapest Treaty and assigned accession number DSM 34119.

The present disclosure also provides a method for producing butyric acid, which includes cultivating an isolated strain of *Roseburia hominis* HGM001 in a culture medium containing a fermentable sugar.

As used herein, the term "fermentable sugar" refers to any sugar that can be used as carbon sources by microorganisms in a fermentation reaction, including monosaccharides, disaccharides, and polysaccharides.

According to the present disclosure, the fermentable sugar may be selected from the group consisting of glucose, xylose, galactose, lactose, cellobiose, sucrose, maltose, starch, glycogen, cellulose, and combinations thereof.

According to the present disclosure, the culture medium may further contain 1 mM to 2 mM of isobutyric acid. In an exemplary embodiment, the culture medium may contain 1.28 mM of isobutyric acid.

According to the present disclosure, the culture medium may be purchased commercially or self-prepared using standard techniques well known to those skilled in the art. Examples of the culture medium may include, but are not limited to, yeast extract-casitone-glucose (YCG) broth, yeast extract-casitone-fatty acid (YCFA) broth supplemented with glucose (G)(also known as YCFAG broth), and YCFA broth supplemented with glucose, maltose, and cellobiose (GSC)(also known as YCFAGSC broth).

As used herein, the term "cultivating" can be used interchangeably with other terms such as "fermentation" and "culturing".

It should be noted that the procedures and operating conditions for cultivating the isolated strain of *Roseburia hominis* HGM001 may be adjusted according to practical requirements. In this regard, those skilled in the art may refer to patents and journal articles, e.g., Duncan, S. H. et al. (2002), supra, and WO 2017033925 A1.

In certain embodiments, cultivation may be conducted at 37° C. for a time period ranging from 24 hours to 72 hours. In an exemplary embodiment, cultivation is conducted at 37° C. for 48 hours.

In certain embodiments, cultivation may be conducted by cultivating the isolated strain of *Roseburia hominis* HGM001 in an amount of $1 \times 10^6$ CFU/mL to $4 \times 10^9$ CFU/mL in the culture medium. In an exemplary embodiment, the isolated strain of *Roseburia hominis* HGM001 is cultivated in an amount of $1 \times 10^8$ CFU/mL to $4 \times 10^9$ CFU/mL in the culture medium.

The present disclosure provides a fermented culture including butyric acid, which is produced by the abovementioned method.

In certain embodiments, the fermented culture is a liquid culture.

In certain embodiments, the liquid culture may be substantially free of cells.

As used herein, the term "substantially free of" means that the liquid culture lacks a significant amount of a specified component (i.e., bacterial cells). In certain embodiments, the amount of the bacterial cells does not have a measurable effect on the properties of the liquid culture. In other embodiments, the liquid culture is completely free of the bacterial cells.

According to the present disclosure, the liquid culture which is substantially free of cells may be obtained by subjecting a fermented culture formed after cultivating the isolated strain of *Roseburia hominis* HGM001 to a separation treatment to remove bacterial cells therefrom.

According to the present disclosure, the separation treatment may be performed using techniques well-known to those skilled in the art. Examples of the separation treatment may include, but are not limited to, filtration, centrifugation, and a combination thereof.

In an exemplary embodiment, the liquid culture which is substantially free of cells is obtained by subjecting the fermented culture formed after cultivating the isolated strain of *Roseburia hominis* HGM001 to a centrifugation treatment, followed by a filtration treatment.

Moreover, the present disclosure provides a method for alleviating an inflammatory disorder, which includes administering to a subject in need thereof a composition including the aforesaid fermented culture.

As used herein, the term "alleviating" or "alleviation" refers to at least partially reducing, ameliorating, relieving, controlling, treating or eliminating one or more clinical signs of a disease or disorder; and lowering, delaying, stopping or reversing the progression of severity regarding the condition or symptom being treated and preventing or decreasing the likelihood or probability thereof.

As used herein, the term "administering" or "administration" means introducing, providing or delivering the abovementioned composition to a subject showing condition(s) or symptom(s) of an inflammation-related disorder by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human.

According to the present disclosure, the inflammatory disorder may be selected from the group consisting of inflammatory bowel disease (IBD), irritable bowel syndrome (IBS), and a combination thereof.

According to the present disclosure, the composition may be formulated as a food product using a standard technique well known to one of ordinary skill in the art. For example, the composition may be directly added to an edible material or may be used to prepare an intermediate composition (e.g., a food additive or a premix) suitable to be subsequently added to the edible material.

As used herein, the term "food product" refers to any article or substance that can be ingested by a subject into the body thereof. Examples of the food product may include, but are not limited to, fluid milk products (e.g., milk and concentrated milk), fermented milk (e.g., yogurt, sour milk, and frozen yogurt), milk powder, ice cream, cream cheese, dry cheese, soybean milk, fermented soybean milk, vegetable fruit juice, fruit juice, sport drinks, confectionery, jelly, candies, health foods, animal feeds, feed additives, and dietary supplements.

According to the present disclosure, the composition may be prepared in the form of a pharmaceutical composition. The pharmaceutical composition may be formulated into a suitable dosage form for oral or parenteral administration using technology well known to those skilled in the art.

According to the present disclosure, the suitable dosage form for oral administration includes, but is not limited to, sterile powders, tablets, troches, lozenges, pellets, capsules, dispersible powders or granules, solutions, suspensions, emulsions, syrup, elixir, slurry, and the like.

For parenteral administration, the pharmaceutical composition according to the present disclosure may be formulated into an injection, e.g., a sterile aqueous solution or a dispersion.

The pharmaceutical composition according to the present disclosure may be administered via one of the following parenteral routes: intraperitoneal injection, intrapleural injection, intramuscular injection, intravenous injection, intraarterial injection, intraarticular injection, intrasynovial injection, intrathecal injection, intracranial injection, intraepidermal injection, subcutaneous injection, intradermal injection, intralesional injection, and sublingual administration.

The pharmaceutical composition according to the present disclosure may further include a pharmaceutically acceptable carrier widely employed in the art of drug-manufacturing. For instance, the pharmaceutically acceptable carrier may include one or more of the following agents: solvents, buffers, emulsifiers, suspending agents, decomposers, disintegrating agents, dispersing agents, binding agents, excipients, stabilizing agents, chelating agents, diluents, gelling agents, preservatives, fillers, wetting agents, lubricants, absorption delaying agents, liposomes, and the like. The choice and amount of the aforesaid agents are within the expertise and routine skills of those skilled in the art.

The dose and frequency of administration of the composition according to the present disclosure may vary depending on the following factors: the severity of the illness or disorder to be treated, routes of administration, and age, physical condition and response of the subject to be treated. In general, the composition may be administered in a single dose or in several doses.

The present disclosure will be further described by way of the following examples. However, it should be understood that the following examples are intended solely for the purpose of illustration and should not be construed as limiting the present disclosure in practice.

EXAMPLES

General Experimental Materials:

1. Yeast extract-casitone-glucose (YCG) broth used in the following experiments was prepared according to the procedures described in WO 2017033925 A1.

2. Yeast extract-casitone-fatty acid (YCFA) broth supplemented with glucose (G) (which is referred to as "YCFAG broth" hereinafter) was prepared according to the procedures described in Duncan, S. H. et al. (2002), supra, and Lopez-Siles, M. et al. (2012), *Appl. Environ. Microbiol.*, 78:420-428.

3. YCFA broth supplemented with glucose, maltose, and cellobiose (GSC) (which is referred to as "YCFAGSC broth" hereinafter) was prepared by adding 2 g/L of cellobiose and 2 g/L of maltose to YCFAG broth.

4. YCFAGSC agar medium used in the following experiments was prepared by adding 18 g/L of agar to YCFAGSC broth.

5. Human colon adenocarcinoma cell line Caco-2

Human colon adenocarcinoma cell line Caco-2 was purchased from the Bioresource Collection and Research Center (BCRC) of the Food Industry Research and Development Institute (FIRDI) (No. 331, Shih-Pin Rd., Hsinchu City 300, Taiwan). The Caco-2 cells were grown in a 10-cm Petri dish containing Eagle's Minimum Essential Medium (EMEM) (Gibco BRL) supplemented with 20% fetal bovine serum (FBS). The Caco-2 cells were cultivated in an incubator with culture conditions set at 37° C. and 5% $CO_2$. Medium change was performed every two to three days. Cell passage was performed when the cultured cells reached 90% of confluence.

General Procedures:

A. Statistical Analysis

The experimental data are expressed as mean±standard deviation (SD). All the data were analyzed using paired Student's t-test, so as to evaluate the differences between the groups. Statistical significance is indicated by $p<0.05$.

Example 1. Screening and Characteristic Analysis of Enteric Bacterial Isolate HGM001

A. Preliminary Screening of Enteric Bacterial Isolate HGM001

Feces of a healthy subject was subjected to a homogenization treatment with a homogenizer (ULTRA-TURRAX® Tube Drive, IKA) under an anaerobic condition. The resultant homogenized mixture was subjected to serial dilution with a 0.85% saline solution, so as to obtain 7 dilutions (prepared using dilution factors of $10^1$, $10^2$, $10^3$, $10^4$, $10^5$, $10^6$, and $10^7$). 0.2 mL of a respective one of the two dilutions (i.e., $10^6$ and $10^7$) was evenly spread onto YCFAGSC agar medium, and was then cultured under an anaerobic condition at 37° C. for 72 hours.

An enteric bacterial isolate was randomly selected from the YCFAGSC agar medium, and was designated as HGM001. The enteric bacterial isolate HGM001 was subjected to the following analyses.

B. Morphological Analysis

The enteric bacterial isolate HGM001 was subjected to morphological analysis using a scanning electron microscope (S-4700, Hitachi).

Referring to FIG. 1, the enteric bacterial isolate HGM001 was motile, and the cells of the enteric bacterial isolate HGM001 were rod-shaped and had a size ranging from 0.4 μM to 3.9 μM.

C. Analysis of Enzymatic Activity

The enteric bacterial isolate HGM001 was subjected to enzymatic activity analysis using API® ZYM system (bioMérieux) in accordance with the manufacturer's instructions. The result is shown in Table 1 below.

TABLE 1

| Enzyme | Possession of activity thereof |
|---|---|
| Alkaline phosphatase | + |
| Esterase (C4) | + |
| Esterase lipase (C8) | + |
| Lipase (C14) | − |
| Leucine arylamidase | + |
| Valine arylamidase | − |
| Cystine arylamidase | − |
| Trypsin | − |
| α-Chymotrypsin | − |
| Acid phosphatase | + |
| Naphthol-AS-BI-phosphohydrolase | + |
| α-Galactosidase | + |
| β-Galactosidase | + |
| β-Glucuronidase | + |
| α-Glucosidase | + |
| β-Glucosidase | + |
| N-Acetyl-β-glucosaminidase | − |
| α-Mannosidase | − |
| α-Fucosidase | − |

Note:
"+" indicates that the enteric bacterial isolate HGM001 has the enzymatic activity tested, whereas "−" indicates that such isolate has no enzymatic activity tested.

D. Analysis of Fatty Acid Components

The enteric bacterial isolate HGM001 was subjected to determination of fatty acid components and their contents using a method slightly modified from that described by Chern, L. L. et al. (2004), *Int. J. Syst. Evol. Microbiol.*, 54:1387-1391. Briefly, methylated fatty acids were extracted from the enteric bacterial isolate HGM001 using MIDI Sherlock® microbial identification system (MIDI Inc.), followed by conducting gas chromatography (GC) analysis with Hewlett Packard HP 5890 Series II gas chromatography system according to the manufacturer's instructions.

The operating parameters and conditions for performing GC analysis are summarized in Table 2 below.

TABLE 2

| | |
|---|---|
| Type of chromatography column | J&W Ultra 2 GC Column (Agilent, Cat. No. 19091B-102) |
| Size of chromatography column | Length: 30 m; inner diameter: 0.25 mm; film thickness: 0.25 μm |
| Temperature of column oven | Initial temperature: 295° C. for 10 minutes; injection temperature: 190° C.; operating temperature: 285° C. (10° C./minute) and 310° C. (60° C./minute) for 0.42 minutes |
| Carrier gas | $H_2$ |
| Injector | G1512A controller |
| Temperature of injector | 250° C. |
| Detector | Flame ionization detector (FID) |
| Temperature of detector | 300° C. |
| Injection volume of test sample | 2 μL |

As shown in Table 3 below, the major fatty acids of the enteric bacterial isolate HGM001 were C16:0, C17:0 iso, C17:0, and C16:1 iso H.

TABLE 3

| Type of fatty acid | Content (%) |
|---|---|
| C16:0 | 26.1 ± 0.68 |
| C17:0 iso | 17.0 ± 0.53 |
| C17:0 | 13.6 ± 0.84 |
| C16:1 iso H | 14.3 ± 0.5 |
| C16:1 2OH | 6.5 ± 0.3 |
| C16:0 N alcohol | 4.6 ± 0.17 |
| C13:1 at 12-13 | 2.9 ± 0.24 |
| 16:0 iso | 2.6 ± 0.03 |
| 18:00 | 1.9 ± 0.21 |
| C15:0 iso | 1.0 ± 0.08 |
| Summed feature 1 | 6.6 ± 0.65 |

Note:
summed feature 1 contained C15:1 iso H/13:0 3OH or C13:0 3OH/15:1 iso H.

E. Protein Fingerprinting Analysis

The enteric bacterial isolate HGM001 was subjected to protein fingerprinting analysis with a matrix-assisted laser desorption ionization-time of flight (MALDI-TOF) mass spectrometer (Microflex LT, Bruker) using a method slightly modified from that described by Lagier, J. C. et al. (2012), Clin. Microbiol. Infect., 18:1185-1193, so as to identify the bacterial species of the enteric bacterial isolate HGM001.

Figure 2:
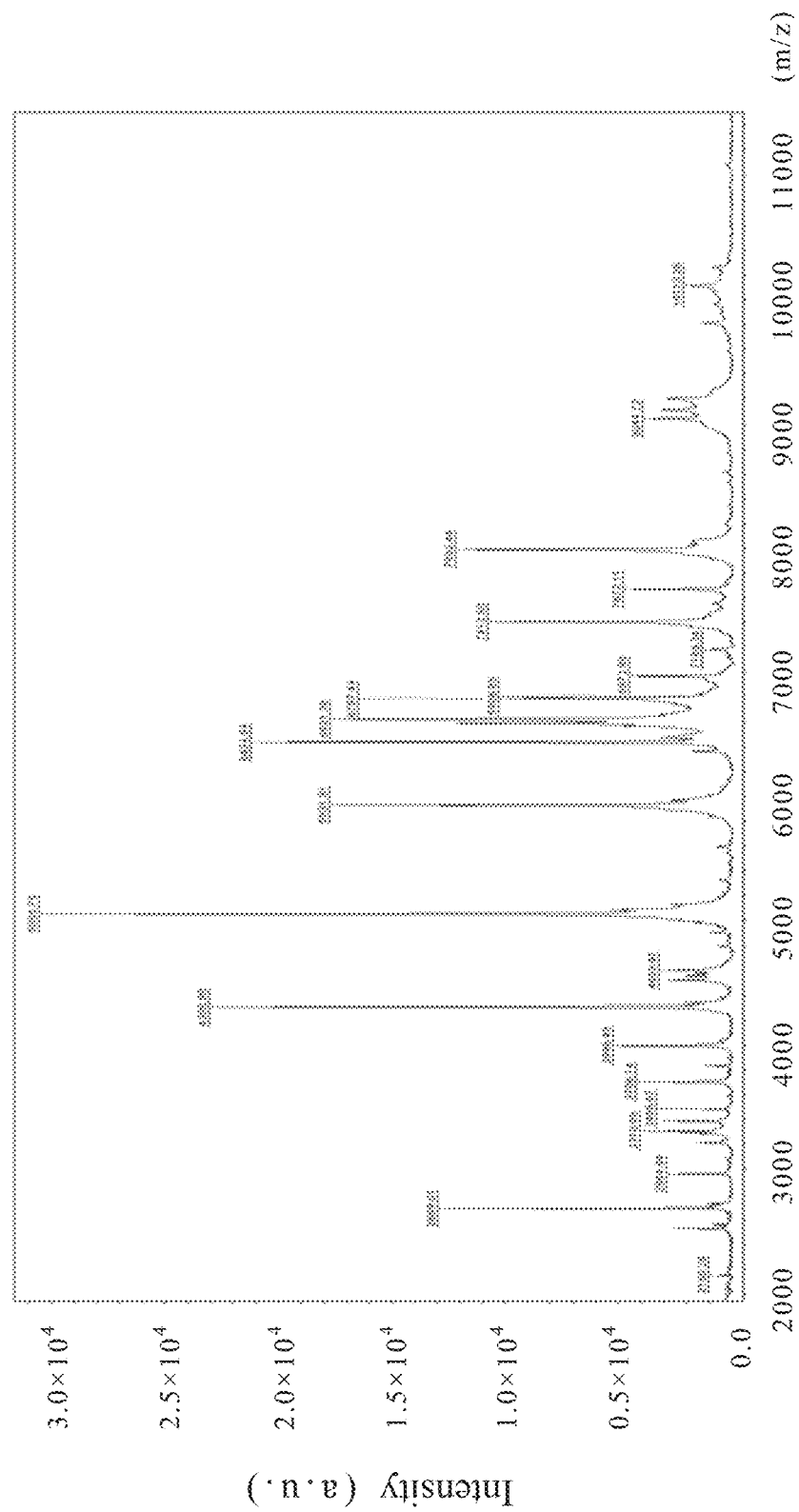
FIG. 2 shows a protein fingerprinting profile of the enteric bacterial isolate HGM001.

FIG. 2 shows the protein fingerprinting profile of the enteric bacterial isolate HGM001. The aforesaid protein fingerprinting profile was subjected to comparison with the data in the MALDI Biotyper® microbial identification system, and it was found that the protein fingerprinting profile of the enteric bacterial isolate HGM001 of the present disclosure has high identity (score value is 2.59) to that of Roseburia hominis A2-183$^T$ (corresponding to strain JCM 17582, strain DSM 16839$^T$ disclosed in WO 2017033925 A1, and strain A2-183 disclosed in Duncan, S. H. et al. (2002), supra).

F. 16S rDNA Sequence Analysis

Genomic DNA of the enteric bacterial isolate HGM001 was extracted using FavorPrep™ Blood Genomic DNA Extraction Mini Kit (Favorgen, Cat. No. FABGK300). The thus obtained genomic DNA was used as a template and was subjected to polymerase chain reaction (PCR) that was performed using the designed primer pair specific for 16S ribosomal DNA (rDNA) and the reaction conditions shown in Table 4, thereby obtaining a PCR product having a size of approximately 1,480 bp.

TABLE 4

| Contents | | Volume (μL) |
|---|---|---|
| Genomic DNA of enteric bacterial isolate HGM001 (50-100 ng) | | 2 |
| 16S rDNA-specific primer pair | Forward primer 8F (100 pM): 5'-ggagtttgatcctggctcag-3' (SEQ ID No: 1) | 2.4 |
| | Reverse primer 1540R (100 pM): 5'-aaggaggtgatccagcc-3' (SEQ ID No: 2) | 2.4 |
| dNTPs (200 μM) | | 1.2 |
| 10X buffer | | 9 |
| Tag DNA polymerase (2.5 U/μL) | | 0.5 |
| dd$H_2$O | | 72.5 |

Operation conditions: denaturation at 94° C. for 5 min, followed by 30 cycles of the following reactions: denaturation at 94° C. for 1 min, primer annealing at 60° C. for 1 min, and extension at 72° C. for 7 min.

The resultant PCR product was subjected to 2% agarose gel electrophoresis analysis for molecular weight verification.

Thereafter, the PCR product was verified by sequencing analysis which was entrusted to Mission Biotech Co., Ltd., Taiwan, so as to obtain the 16S rDNA sequence (SEQ ID No: 3) of the enteric bacterial isolate HGM001. Through comparison with the data in the EzBioCloud's 16S database and the NCBI's gene database, it was found that the 16S rDNA sequence of the enteric bacterial isolate HGM001 has 100% identity to that of Roseburia hominis A2-183$^T$ (GenBank accession number CP003040.1).

In view of the aforesaid experimental results, the enteric bacterial isolate HGM001 of the present disclosure is identified as Roseburia hominis. In order to confirm whether Roseburia hominis strain HGM001 (i.e. the enteric bacterial isolate HGM001) is a novel Roseburia hominis strain, the following experiment was conducted.

G. Phylogenetic Analysis

The genomic DNA of Roseburia hominis strain HGM001 obtained in section F of this example was subjected to sonication, so as to form DNA fragments having a size of 350 bp. Next, a DNA library of Roseburia hominis strain HGM001 was prepared using the DNA fragments and NEBNext® Ultra™ DNA Library Prep Kit for Illumina® (New England Biolabs Inc., Ipswich, Mass.) in accordance with the manufacturer's instructions. Thereafter, the DNA library was subjected to next-generation sequencing (NGS) analysis which was entrusted to Tri-I Biotech, Inc., Ltd., Taiwan, so as to obtain a full-length genomic DNA sequence of Roseburia hominis strain HGM001 (3,533,908 bp).

Through comparison with the data in the NCBI's gene database and the data in the EzBioCloud's database, it was found that the full-length genomic DNA sequence of Roseburia hominis strain HGM001 is most homologous to that of Roseburia hominis A2-183$^T$, to that of Roseburia hominis AF22-12AC, and to that of Roseburia intestinalis L1-82$^T$ (corresponding to strain DSM 14610$^T$).

Thereafter, the full-length genomic DNA sequence of each of *Roseburia hominis* strain HGM001, *Roseburia hominis* A2-183$^T$, *Roseburia hominis* AF22-12AC, and *Roseburia intestinalis* L1-82$^T$ was compared and analyzed using Orthologous Average Nucleotide Identity Tool (OAT) software, followed by conducting phylogenetic analysis using Molecular Evolutionary Genetics Analysis (MEGA) software (Pennsylvania State University, USA) and the maximum likelihood method, so as to obtain a phylogenetic tree.

Figure 3:
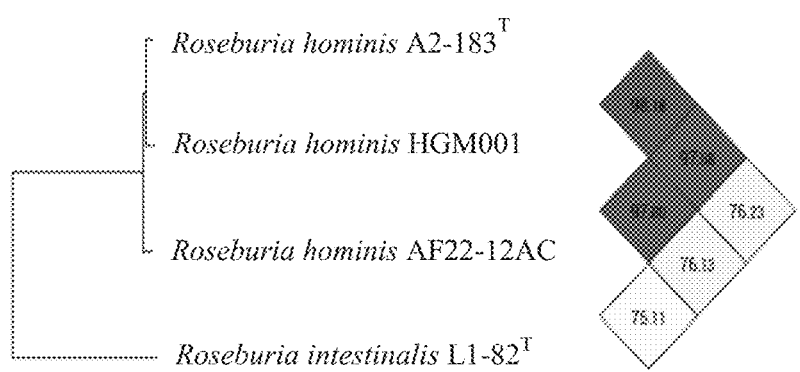
FIG. 3 is a phylogenetic tree based on average nucleotide identity (ANI) analysis.

FIG. 3 is a phylogenetic tree based on average nucleotide identity (ANI) analysis. It can be seen from FIG. 3 that the ANI value between *Roseburia hominis* strain HGM001 and *Roseburia hominis* A2-183$^T$ was 98.18%.

Based on the aforementioned characterization results, the applicant believes that the *Roseburia hominis* strain HGM001 is a novel strain of *Roseburia hominis*. As such, *Roseburia hominis* strain HGM001 has been deposited at the Bioresource Collection and Research Center (BCRC) of the Food Industry Research and Development Institute (FIRDI) (No. 331, Shih-Pin Rd., Hsinchu City 300, Taiwan) under an accession number BCRC 911054 since Apr. 20, 2021, and has also been deposited at the Deutsche Sammlung von Mikroorganismen und Zellkulturen (DSMZ) GmbH (Inhoffenstraße 7B, 38124 Braunschweig, Germany) under an accession number DSM 34119 since Jan. 10, 2022 in accordance with the Budapest Treaty.

Example 2. Evaluation of the Effect of *Roseburia hominis* HGM001 on Production of Butyric Acid A. Preparation of Inoculum of *Roseburia hominis* HGM001

*Roseburia hominis* strain HGM001 obtained in Example 1 was inoculated in an amount of 0.1% (v/v) into a YCF-AGSC broth, followed by cultivation in a Vinyl Anaerobic Chamber (Coy Laboratory products) at 37° C. for 24 hours, so as to obtain an inoculum of *Roseburia hominis* strain HGM001.

B. Preparation of Fermented Culture of *Roseburia hominis* HGM001

The inoculum of *Roseburia hominis* strain HGM001 prepared in section A of this example was divided into three experimental groups (i.e., experimental groups 1 to 3). Each group of the inoculum was subjected to anaerobic cultivation in an incubator (37° C.) according to the culture conditions shown in Table 5, so as to obtain a respective fermented culture.

TABLE 5

| Group | Culture medium | Time period (hour) | Amount of inoculum (CFU/mL) |
|---|---|---|---|
| Experimental group 1 | YCG broth | 72 | 1 × 10$^6$ |
| Experimental group 2 | YCFAG broth | 24 | |
| Experimental group 3 | YCFAGSC broth | 48 | |

Note:
the culture conditions for the experimental group 1 are applied in WO 2017033925 A1, and the culture conditions for the experimental group 2 are applied in Duncan, S.H. et al. (2002), supra.

C. Determination of Butyric Acid Content 0.5 g of the fermented culture of the respective experimental group prepared in section B of this example was mixed with ddH$_2$O to reach a final volume of 5 mL, followed by conducting filtration using a filter (pore size: 0.45 μm) (UNI-ONWARD Corporation) to obtain a test sample, and then high performance liquid chromatography (HPLC) analysis, so as to determine the butyric acid content therein.

HPLC analysis was performed using a Chromaster HPLC system (HITACHI) equipped with a Hitachi CM 5110 pump and a Hitachi CM 5420 UV-VIS detector and the operating conditions shown in Table 6 below.

TABLE 6

| | |
|---|---|
| Type of column | Aminex HPX-87H (BioRad) |
| Size of column | Length: 300 mm; inner diameter: 7.8 mm |
| Column temperature | 50° C. |
| Sample injection volume | 20 μL |
| Detection wavelength | UV-210 nm |
| Mobile phase | 0.009N H$_2$SO$_4$ (pH 2.3) |
| Flow rate | 0.6 mL/min |

In addition, butyric acid was used as a control standard (which was purchased from Sigma-Aldrich and which was provided at concentrations of 1, 2, 5, 10, 20, and 50 mg/mL), and was subjected to the same HPLC analysis, so as to prepare a standard curve.

As shown in Table 7 below, satisfactory contents of butyric acid were found in the experimental groups 1 to 3, indicating that *Roseburia hominis* strain HGM001 can produce butyric acid when cultivated at different culture conditions. In particular, the butyric acid content produced in the fermented culture of the experimental group 1 was significantly higher than that (i.e., 1.0 mM) produced in the fermented culture of *Roseburia hominis* DSM 16839$^T$ disclosed in WO 2017033925 A1, and the butyric acid content produced in the fermented culture of the experimental group 2 was significantly higher than that that (i.e., 11.42 mM) produced in the fermented culture of *Roseburia* spp. strain A2-183 disclosed in Duncan, S. H. et al. (2002), supra. It has been known that strain DSM 16839$^T$ and strain A2-183 correspond to *Roseburia hominis* A2-183$^T$.

The aforesaid result suggests that the content of butyric acid produced by *Roseburia hominis* strain HGM001 is higher than that produced by *Roseburia hominis* A2-183$^T$ when cultivated at the same culture conditions.

TABLE 7

| Group | Butyric acid content (mM) |
|---|---|
| Experimental group 1 | 18.5 ± 0.4 |
| Experimental group 2 | 28.2 ± 0.3 |
| Experimental group 3 | 80.6 ± 1.2 |

Example 3. Evaluation of the Effect of *Roseburia hominis* HGM001 on Alleviating Inflammation-Induced Intestinal Barrier Dysfunction A. Preparation of Filtrate Containing Butyric Acid The inoculum of *Roseburia hominis* strain HGM001 prepared in section A of Example 2 was evenly spread onto YCFAGSC agar medium, followed by conducting fermentation under an anaerobic condition at 37° C. for 24 hours. A suitable amount of the bacterial cells containing butyric acid were taken from the YCFAGSC agar medium by a platinum loop, and were then suspended in 20 mL of Eagle's Minimum Essential Medium (EMEM) (Gibco BRL) supplemented with 1% penicillin-streptomycin, so as to obtain a bacterial suspension having a bacterial concentration of $4\times10^9$ CFU/mL ($OD_{600}$ value=2). The resultant bacterial suspension was fully stirred, so that butyric acid was released from the bacterial cells of Roseburia hominis strain HGM001.

After centrifugation at 4,000 rpm for 15 minutes, the resultant supernatant was collected, followed by conducting filtration using a filter (pore size: 0.22 µm) (UNI-ONWARD Corporation) to obtain a filtrate containing butyric acid.

B. Transepithelial Electrical Resistance (TEER) Assay

A Caco-2 cell monolayer was prepared using a method slightly modified from that described by Hsieh, C. Y. et al. (2015), *Physiol. Rep.*, doi: 10.14814/phy2.12327, and TEER assay was conducted using a method slightly modified from that described by Cocetta, V. et al. (2019), *Recent Pat. Food Nutr. Agric.*, 10:62-69. Specifically, the Caco-2 cells prepared in section 5 of "General Experimental Materials" were divided into 3 groups, including one normal control group, one pathological control group, and one experimental group. Each group of the Caco-2 cells was seeded at a concentration of $1\times10^5$ cells per well into respective permeable Transwell® insert (Corning Inc.) for a 12-well plate. Each of the Transwell® inserts had a polycarbonate membrane (pore size: 0.4 µm). Next, the Transwell® inserts were placed into the 12-well plate that contained 1.5 mL of EMEM in each well, followed by cultivation in an incubator (37° C., 5% $CO_2$) for 3 weeks to 4 weeks, so that the Caco-2 cells formed a cell monolayer in the Transwell® inserts.

Thereafter, the Caco-2 cell monolayer of the experimental group was treated with 50 µL of the filtrate prepared in section A of this example, and the Caco-2 cell monolayers of the normal control group and pathological control group received no treatment. Each group was cultivated in an incubator (37° C.) for a total of 24 hours.

On the $2^{nd}$ hour after cultivation, the Caco-2 cell monolayers of the experimental group and pathological control group were added with 10 ng/mL of Interferon-γ (INF-γ) (R&D). After incubation with INF-γ for 3 hours, the Caco-2 cell monolayers of the experimental group and pathological control group were added with 10 ng/mL of tumor necrosis factor-α (TNF-α) (R&D), so as to induce intestinal barrier dysfunction.

After the 24-hour cultivation period, each group was subjected to determination of TEER level using a Millicell® ERS-2 voltohmmeter in accordance with the manufacturer's instructions. The relative TEER level (%) of each group was calculated by substituting the thus determined TEER level into the following Equation (I):

$$A=(B/C)\times100 \qquad (I)$$

where
A=relative TEER level (%)
B=TEER level of respective group
C=TEER level of normal control group The data thus obtained were analyzed according section 1 of "General Procedures".

Figure 4:
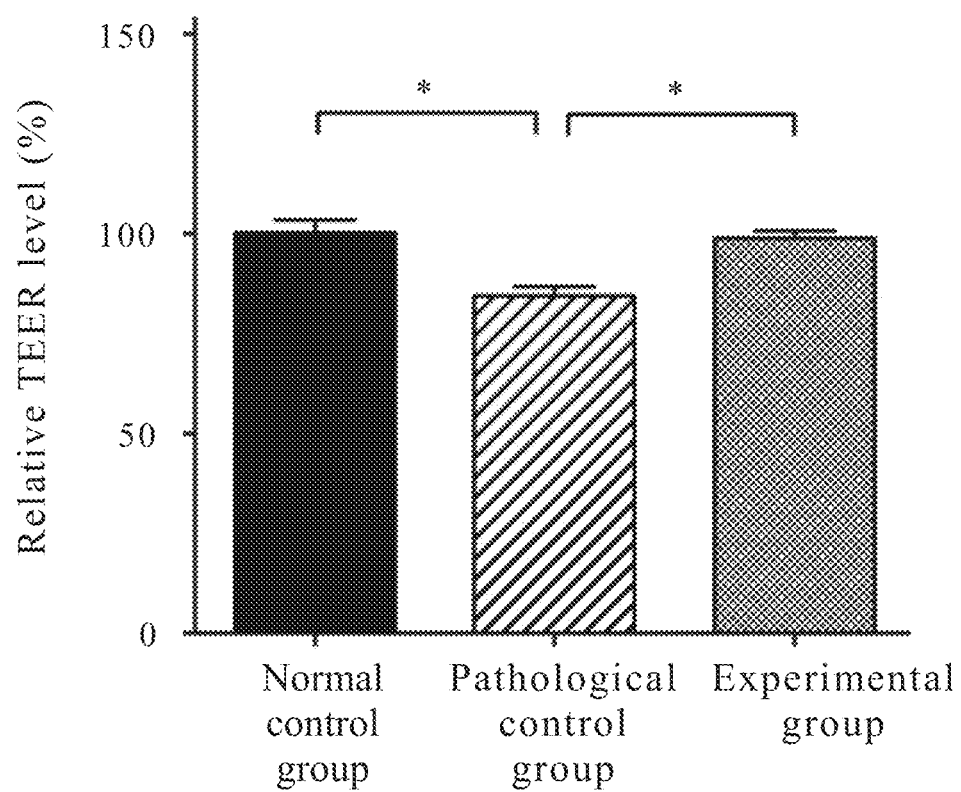
FIG. 4 shows a relative transepithelial electrical resistance (TEER) level in each group of Example 3, infra, in which the symbol "*" represents p<0.05 (compared with the pathological control group).

Referring to FIG. 4, the relative TEER level determined in the pathological control group was significantly lower than that determined in the normal control group, indicating that intestinal barrier dysfunction was successfully induced by INF-γ and TNF-α in the Caco-2 cell monolayer. In addition, the relative TEER level determined in the experimental group was significantly higher than that determined in the pathological control group, indicating that the filtrate, which contains butyric acid and other metabolites released from the bacterial cells of Roseburia hominis strain HGM001 after fermentation, can effectively alleviate intestinal inflammation.

Summarizing the above test results, it is clear that *Roseburia hominis* HGM001 of the present disclosure has an excellent butyric acid production capability, and the fermented culture of *Roseburia hominis* HGM001 is capable of alleviating an inflammatory disorder.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for producing butyric acid, comprising cultivating an isolated strain of *Roseburia hominis* HGM001 in a culture medium containing a fermentable sugar,
wherein the isolated strain of *Roseburia hominis* is strain HGM001 deposited at Deutsche Sammlung von Mikroorganismen und Zellkulturen GmbH under accession number DSM 34119.

2. The method as claimed in claim 1, wherein the fermentable sugar is selected from the group consisting of glucose, xylose, galactose, lactose, cellobiose, sucrose, maltose, starch, glycogen, cellulose, and combinations thereof.

* * * * *